United States Patent
Biellak et al.

(10) Patent No.: US 8,169,613 B1
(45) Date of Patent: May 1, 2012

(54) SEGMENTED POLARIZER FOR OPTIMIZING PERFORMANCE OF A SURFACE INSPECTION SYSTEM

(75) Inventors: Stephen Biellak, Sunnyvale, CA (US); Daniel Kavaldjiev, San Jose, CA (US)

(73) Assignee: KLA-Tencor Corp., San Jose, CA (US)

( * ) Notice: Subject to any disclaimer, the term of this patent is extended or adjusted under 35 U.S.C. 154(b) by 347 days.

(21) Appl. No.: 12/618,620

(22) Filed: Nov. 13, 2009

Related U.S. Application Data

(60) Provisional application No. 61/117,006, filed on Nov. 21, 2008.

(51) Int. Cl.
*G01J 4/00* (2006.01)
(52) U.S. Cl. ............ 356/369; 356/237.2; 356/237.5
(58) Field of Classification Search .......... 356/364–369, 356/237.2–237.5
See application file for complete search history.

(56) References Cited

U.S. PATENT DOCUMENTS

| | | | |
|---|---|---|---|
| 7,221,501 B2 * | 5/2007 | Flagello et al. | 359/352 |
| 7,436,505 B2 * | 10/2008 | Belyaev et al. | 356/237.2 |
| 7,623,229 B1 * | 11/2009 | Vaez-Iravani et al. | 356/237.5 |
| 7,912,658 B2 * | 3/2011 | Biellak et al. | 702/40 |
| 2005/0110986 A1 * | 5/2005 | Nikoonahad et al. | 356/237.2 |
| 2007/0229833 A1 * | 10/2007 | Rosencwaig et al. | 356/426 |
| 2010/0188657 A1 * | 7/2010 | Chen et al. | 356/237.5 |

* cited by examiner

*Primary Examiner* — Layla Lauchman
(74) *Attorney, Agent, or Firm* — Joshua D. Isenberg; JDI Patent

(57) ABSTRACT

A polarizing device may be used with sample inspection system having one or more collection systems that receive scattered radiation from a region on a sample surface and direct it to a detector. The polarizing device disposed between the collection system(s) and the detector. The polarizing device may include a plurality of polarizing sections. The sections may be characterized by different polarization characteristics. The polarizing device is configured to transmit scattered radiation from defects to the detector and to block noise from background sources that do not share characteristics with scattered radiation from the defects from reaching the detector while, maximizing a capture rate for the defects the detector at a less than optimal signal-to-noise ratio.

18 Claims, 6 Drawing Sheets

SEGMENTED POLARIZER FOR OPTIMIZING PERFORMANCE OF A SURFACE INSPECTION SYSTEM

CLAIM OF PRIORITY

This applications claims the priority benefit of U.S. Provisional Patent Application No. 61/117,006, filed Nov. 21, 2008, the entire contents of which are incorporated herein by reference.

FIELD OF THE INVENTION

This invention relates to polarizing devices used in conjunction with sample inspection systems to increase sensitivity towards particulates and other small defects of the sample.

BACKGROUND

Optical scattering techniques are in wide use for inspecting highly polished surfaces, such as those of lenses and silicon wafers as employed as starting materials in semiconductor manufacture. These techniques involve directing a monochromatic beam of incident light onto the surface. Most of the beam is "specularly" reflected, that is, is reflected at an angle of reflection equal to the angle of incidence; however, a small fraction of the beam is "scattered" into other directions. The amount of light scattered is generally representative of the roughness of the surface and the presence of particulates thereon, or defects therein.

Optical scattering techniques provide a powerful tool for process monitoring in manufacturing environments because of their non-contact nature and relative ease of use. For example, optical scattering techniques are often employed to detect particulate contamination of silicon wafers on fabrication lines. The requirement that particles smaller than the minimum dimension of the features to be fabricated on the wafer, which can be reliably detected, places strict demands on the sensitivity of an instrument to those particles. One important issue that limits the sensitivity of such an instrument to particulates and other small defects is the noise associated with the scattering signal due to background sources including surface microroughness.

The full strength of the optical scattering technique lies in its ability to diagnose deviations from ideal conditions. For example, optical scattering from smooth surfaces, such as mirrors, transparent optics, and silicon wafers can yield information about the condition of those surfaces. Surface microroughness, particulate contamination, and subsurface defects result from different adverse conditions in the manufacturing environment; distinguishing between these sources of defects can result in improvements in the ability to identify and correct the sources of such conditions.

Current scanning surface inspection systems employ optical scattering techniques to detect microroughness, particles, and defects in silicon wafers. Light is focused onto the surface of the wafer, and optics collect light that is scattered by the surface and image it onto a sensitive detector. Some degree of noise, whether it is from microroughness of the surface of the sample or from some other source, is always present in the scattered radiation signal. This noise has a tendency to hide detection of the smallest particles and defects. Reduction of this noise improves the systems ability to detect smaller particulates and defects.

U.S. Pat. No. 6,034,776 (hereinafter, the '776 patent) discloses a microroughness-blind optical scanner that focuses p-polarized light onto a surface of a sample. Scattered light is collected through independently rotatable polarizers by one or more collection systems uniformly distributed into several regions over a hemispherical shell centered over the sample. In each separate collector region, a unique linear polarizer is adjusted to a specific angle that nulls or minimizes the microroughness-induced scatter in that region for a given surface to be inspected.

U.S. patent application Ser. No. 11/110,383, filed Apr. 20, 2005, the contents of which are incorporated herein by reference, discloses an inspecting system including an illumination subsystem configured to direct light to the specimen at an oblique angle of incidence. The light is polarized in a plane that is substantially parallel to the plane of incidence. The system also includes a detection subsystem configured to detect light scattered from the specimen. The detected light is polarized in a plane that is substantially parallel to the plane of scattering. This prior art teaches a "pizza-pie-polarizer" 310 as shown in FIG. 3A. The polarizer 310 is a segmented polarizer formed of multiple sections 312 of linear polarizers butted against each other, each having a different orientation 314 for pass axis.

U.S. Pat. No. 7,221,501 also teaches a radial transverse electric polarizer device including a first layer of material having a first refractive index, a second layer of material having a second refractive index, and a plurality of elongated elements azimuthally and periodically spaced apart, and disposed between the first layer and the second layer. The plurality of elongated elements interact with electromagnetic waves of radiation to transmit transverse electric polarization of electromagnetic waves of radiation.

U.S. Pat. No. 7,436,505 discloses a system for determining a configuration for a light scattering inspection system. The optimal configuration may be further refined by determining the effect that polarizing filter element(s) placed in the path(s) of the detected light will have on the sensitivity of the inspection system. In this manner, in some embodiments, the configuration also includes parameter(s) of one or more linear polarizing filters positioned in the scattering hemisphere. In this manner, the determined optimal configuration may be realized by positioning linear polarizing filters in the opening(s) of an aperture plate. The polarizing filter includes a plurality of segments, each of which is a linear polarizing filter arranged azimuthally in the aperture plate openings, which may be commonly referred to as a "pizza-pie" polarizer. The linear polarizing filters may also be disposed in any location with respect to the openings such that light that passes through the openings also passes through the linear polarizing filters. In other words, the linear polarizing filters do not have to be disposed in the openings, but may be disposed upstream or downstream of the aperture.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

INTRODUCTION

Current scanning surface inspection systems fail to realize that the sensitivity of a system towards small particulates and defects lies in increasing the signal-to-noise ratio of the scattered radiation from small particulates and other defects. These systems often try to increase the sensitivity of their system by minimizing the signal caused by surface microroughness, in hopes of limiting the scattered radiation signal to that of the particulates and other defects. This is not the same as optimizing the signal-to-noise ratio of scattered radiation from small particulates and other defects. Minimizing the surface microroughness, in many cases, also minimizes the desired signal from small particulates or defects. In order to increase the signal-to-noise ratio of scattered radiation from small particulates and other defects and in turn increase the sensitivity of the system, a polarizing device that works to limit the noise, while maintaining the signal strength of particulates and other defects is employed. The increased sensitivity of a sample inspection system towards small particulates and other defects lies in its ability to increase the signal-to-noise ratio of the scattered radiation due to particulates or other defects, which does not necessarily correspond to minimizing the signal caused by surface microroughness.

Sample Inspection Systems

Figure 1:
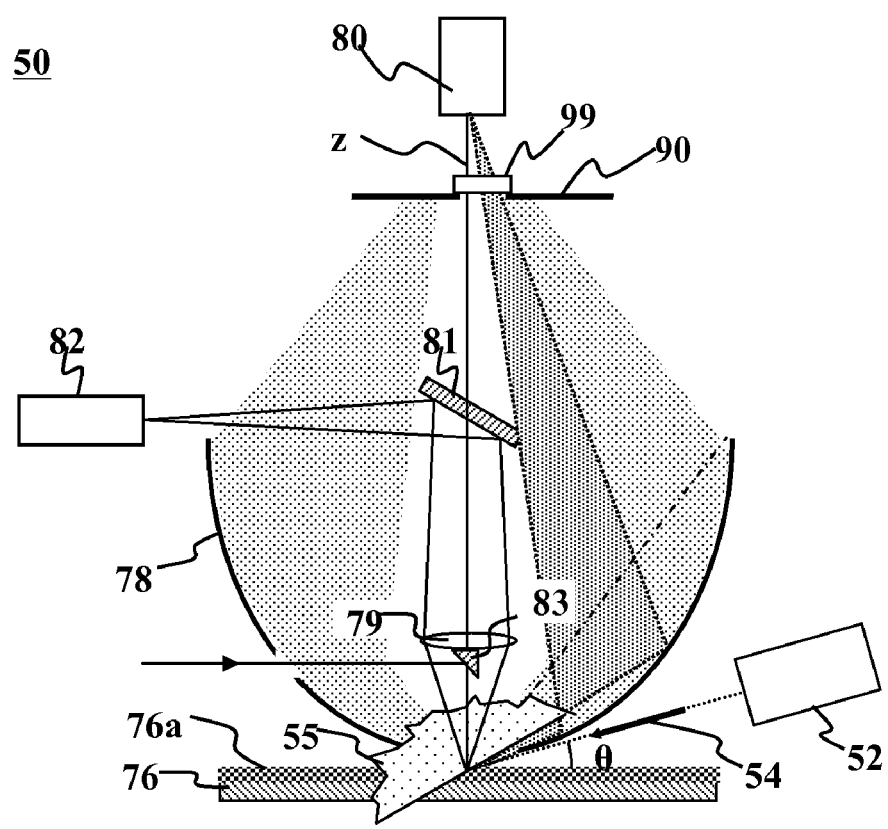
FIG. 1 is a vertical cross-section schematic diagram of a sample inspection system according to an embodiment of the present invention.

Embodiments of the present invention may be implemented in an optical sample inspection system. Such systems may be implemented in a number of ways. An example of such a system is described, e.g., in U.S. Pat. No. 6,201,601, the disclosures of which are incorporated herein by reference. An example of a system of this type is the SP1 from KLA Tencor of Milpitas, Calif. By way of example FIG. 1 is a schematic view of a sample inspection system to illustrate a general set up for a sample inspection system 50 that may be used with embodiments of the present invention. In the system 50, a radiation source 52 may provide incident radiation 54 at one or more wavelengths in a wide electromagnetic spectrum (including but not limited to ultraviolet, visible, infrared). The radiation source 52 may be a laser providing the incident radiation 54 in the form of a laser beam. The system 50 may include two separate radiation sources for normal and oblique illumination of a surface 76a of a sample 76. In the oblique mode, the incident radiation 54 is incident on the surface 76a at an elevation angle θ with respect to the plane of the surface 76a. In some embodiments, the incident angle θ is chosen to be a Brewster angle for the surface 76a so the reflections containing most of the noise may be substantially reduced when a polarized incident radiation 54, e.g., P-polarized, illuminates the surface 76a.

The incident radiation 54 scatters from the surface 76a and the resulting scattered radiation 55 is collected by collection optics, e.g., a curved reflecting surface 78, such as a paraboloidal or ellipsoidal mirror. Curved reflecting surfaces 78 having shapes other than ellipsoidal or paraboloidal shapes may also be used. Preferably, each of such curved reflecting surfaces has symmetry axis z that is substantially coaxial with a normal to the surface 76a at a point where the incident radiation 54 strikes the surface 76a. The symmetry axis z defines an input aperture for receiving scattered radiation 55. There are many other possible configurations for the radiation source, and collections optics. All such variations are within the scope of the invention. The curved reflecting surface 78 directs the scattered radiation 55 to a detector 80, such as a photomultiplier tube. The signal from the detector 80 may be used to generate an image of defects on the surface 76a.

The collection optics may also include a lens 79 and mirror 81 to collect radiation scattered at low angles relative to the symmetry axis z and direct it to a second detector 82. A prism 83 may be located between the lens 79 and the sample to direct incident radiation onto the sample at or near normal incidence, e.g., along the symmetry axis z.

A spatial filter 90 can be located between the collecting optics and the detector. The spatial filter 90 includes one or more portions that are opaque to the scattered radiation. The radiation forward scattered from a rough surfaces mostly contains noise while the backscattered radiation includes both signal and noise. However, in many cases, the noise tends to backscatter from rough surfaces a relatively low angles (e.g., less than about 45° with respect to the normal) and the signal tends to backscatter at relatively higher angles (e.g., greater than about 45°). Thus, to improve the ratio of signal to noise at the detector, the opaque portions of the spatial filter 90 may be configured to block part of the scattered radiation 55 that is primarily forward scattered and allow at least part of the scattered radiation 55 that is primarily backscattered to reach the detector 80. Note that in the embodiment depicted in FIG. 1, the mirror 79 may block some of the low-angle backscattered radiation. It is often the case (though not necessarily the case) that the collection optics cannot collect scattered radiation above some angle with respect to the normal. However, in other cases it may be desirable to optionally configure the spatial filter 90 to block backscattered radiation at elevation angles above some upper limit, e.g., about 75°

Thus forward scattered radiation and low-angle back-scattered radiation may be blocked by appropriate configuration of the opaque and transmitting portions of the spatial filter 90. Appropriate configuration includes, but is not limited to, the size and/or shape of the opaque and transmitting portions of the spatial filter 90, the distance of the spatial filter from the surface 76a and the orientation of the spatial filter, e.g., relative top to the symmetry axis z.

The transmitting portions of the spatial filter 90 may include a polarizing device 99. Alternatively, the polarizing device 99 may be placed along an optical path between the reflecting surface 78 and the detector 80 to intercept light that is directed by the reflecting surface towards the detector. The polarizing device 99 may be designed to function optimally by using the well-known optical properties of a wafer with the same characteristics as a sample that is also known to be perfectly clean and calculating the expected scatter characteristics of the surface and the expected scatter of particle standards, such as polystyrene latex spheres (PSL particles). The spatial-frequency distribution (PSD) of individual surfaces of the same type, for instance, the set of all surfaces that are chemo-mechanically-polished (CMP) copper, may vary to some degree, so the calculations may be somewhat inaccurate, but not by enough to negate their usefulness.

By way of example, the polarizing device may be calibrated to function optimally as follows. Using a simulation tool, similar to the one described in U.S. Pat. No. 7,436,505, referenced above, the polarizing device 99 may be divided into an appropriate number of segments, and the polarization pass axis of each segment is simultaneously varied, also allowing for segments to have no polarizer at all. The smallest particle standard that the polarizing device can reliably capture with each combination of polarizers and pass axes is calculated, and eventually the optimal polarizing device configuration (which is defined as one that is able to capture the smallest particle, or other defect type of interest) is established. Once the SNR of the scattered radiation has been maximized, this signal may be coupled to the detector 80 and then processed to determine where particulates and other defects of a region of the sample 76 are formed. In the absence of a simulation tool, the optimal polarizing device may be determined experimentally, by scanning a particular sample a large number of times while varying the polarizer design, and eventually arriving at the best configuration.

As used herein SNR, or signal to noise ratio, includes not only the noise induced by the surface microroughness scatter, e.g., "haze", but also noise induced in the system by other sources. Obviously, as the '776 patent teaches, if one minimizes the haze, one will minimize the noise from the haze. Haze is, on occasion (but not always), the limiting noise source. However, to maximize the capture rate of particles of a given size, the signal, e.g., the light scattered from a particle, must also be considered. Particles, for instance, often have different scatter characteristics, in terms of the angular direction and angular extent of the scatter, and polarization of the scatter, as compared to surface scattering. Other defects of interest, such as scratches, dimples, line bumps, stacking faults, slip lines, and pits, also scatter differently than surfaces.

U.S. Pat. No. 7,436,505 (hereinafter, the '505 patent) teaches modeling the scattering from a target with defects and determining a map of SNR for the defects. The map of SNR is then used to optimize a configuration of the detection system. However, configuring a detection system to optimize SNR does not necessarily optimize the capture rate of defects unless it also takes into account maximization of the raw signal from the defects.

It is noted that the '505 and '776 patents do not mention capture rate, but extensively discuss reducing the background and/or maximizing signal-to-noise. Based on these teachings alone, one skilled in the art might miss the subtleties of configuring an inspection system to optimize capture rate.

However, as determined by the inventors, it is possible to configure the polarizing device in an inspection system of the type described herein such that a capture rate for the defects by the one or more detectors in the system is maximized at a less than optimal signal-to-noise ratio.

To illustrate this point, consider the following example, suppose that a first configuration of an inspection system produces a Signal of 36 (in arbitary units, say, number of photons received) and an RMS background noise of 6 photons. In this configuration, the SNR is 6:1. Assume, for the sake of example, that this represents an optimal SNR configuration for the polarizing device. Further suppose that a second configuration of the same system produces a Signal of 64 (the same arbitrary units, say, number of photons received) and a RMS background noise of 11 photons. Previous teachings would argue that the first configuration is better since it results in a SNR of 6:1 which is significantly better than the 5.8:1 SNR of the second configuration.

However, it is well known that in a given time interval, a signal will have an RMS noise of $\sqrt{Signal}$. Therefore, for Configuration 1, the average RMS noise of the signal is $\sqrt{36}$, or 6 photons. For Configuration 2, the average RMS noise of the signal is $\sqrt{64}$ or 8 photons. To compare the 95% capture rate of the two Configurations one can use the following formula:

$$95\% \text{ capture rate} \approx \frac{\text{Signal} - 2 \cdot \text{RMS\_nose\_of\_signal}}{\text{RMS\_background\_noise}} \qquad \text{Equation 1}$$

Subtracting twice the RMS noise of the signal from the signal itself assures, with approximately 95% probability, that on any given scan, the signal will remain strong enough to be detected.

The first configuration gives a 95% capture rate of:

$$\frac{(36-12)}{6} = 4:1$$

The second configuration gives a 95% capture rate of:

$$\frac{(64-16)}{11} = 4.36:1$$

Therefore, the second configuration has substantially better capture rate performance (nearly 10% better) despite having an ostensibly worse signal to noise value.

By configuring the polarizing device to allow transmission of more scattered radiation (including more background noise) one can achieve a higher capture rate for particles of interest even though the signal to noise ratio may be significantly less.

The argument works well for relatively modest numbers of signal photons, but indeed, for the smallest defects, given inspection speed requirements, and available levels of laser power, such small numbers of photons can be very realistic. Increasing the defect capture rate by decreasing the SNR, even slightly is, therefore, particularly counterintuitive for small defects.

It is noted that the prior art describes segmented polarizers. For example, U.S. Pat. No. 7,221,501 describes a polarizer in which the polarization direction varies in a radial fashion. The polarizer is made up of multiple segments that are roughly wedge-shaped that are arranged like slices of pizza in a pizza pie. Each segment has a polarization axis that is oriented more or less perpendicular to a line drawn radially from the center of the "pie".

Embodiments of the present invention are not limited to the "pizza pie" geometry described above. An arbitrary number of sections, each section having an arbitrary geometry, and each section having a polarizer oriented at an arbitrary pass axis, or having no polarizer at all, can potentially be determined by a computer algorithm that seeks the maximum signal to noise value for a particular defect type.

Figure 2A:
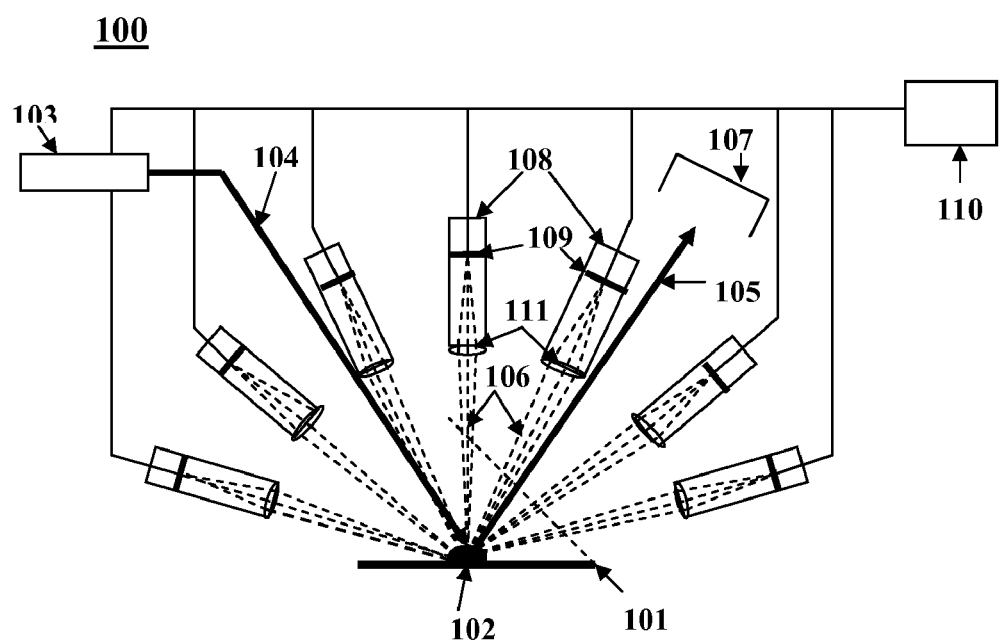
FIG. 2A is a schematic diagram illustrating the overall design of an alternative embodiment of the instrument of the invention, including multiple collection systems.

FIG. 2A is a sample inspection system 100 according to an embodiment of the present invention. A coherent source of light 103 produces a beam of monochromatic incident light 104 onto a region 102 of the sample 101. The incident beam produces specularly reflected radiation 105 as well as scattered radiation 106 due to particulates, microroughness, and other defects present in the region 102 of the sample 101. The specularly reflected light 105 is directed into an efficient beam dump 107 to eliminate stray light. Situated about the region where the incident beam 104 strikes the region 102 of the sample 101 is a plurality of collection systems 108. The collection systems 108 are disposed so as to cover as much of the scattering hemisphere as possible. A lens 111 may be inserted in the front end of the collection system 108 to help focus the scattered light towards a polarizing device 109 situated near the end of the collection system. The polarizing device 109 is divided into a plurality of polarizing segments, wherein each segment is characterized by a different polarization characteristic. The polarization characteristics are selected to transmit scattered radiation from particulates and other defects of the region 102 of the sample 101 and block noise from background sources including scattered radiation from microroughness of the surface of the sample 101 that does not share characteristics with the scatter from particulates or other defects. By doing so, the signal-to-noise ratio (SNR) between the particulate scattering signal and the background sources of noise, which include surface microroughness, can be maximized, and particulates and other defects in the sample 101 may be more accurately identified. Each polarizing device 109 may be calibrated to function optimally by using the well-known optical properties of a wafer with the same characteristics as our sample that is also known to be perfectly clean and calculating the expected scatter characteristics of the surface and the expected scatter of particle standards, such as polystyrene latex spheres (PSL particles). The spatial-frequency distribution (PSD) of individual surfaces may vary to some degree, so the calculations may be somewhat inaccurate, but not by enough to negate their usefulness. Using a simulation tool, or performing a set of experiments on the surface of interest, the polarization pass axis of each segment of each of the polarizing devices 109 may be simultaneously varied, also allowing for some of the devices to have no polarizer at all. It is noted that this is equivalent to the use of a polarizing device having multiple segments with optimally oriented polarizing axes as described above with respect to FIG. 1 and as discussed below with respect to FIG. 2B and FIG. 3B.

The smallest particle standard that the system 100 can reliably capture with each combination of polarizers and pass axes is calculated, and eventually the optimal polarizing device configuration is established. Once the SNR of the scattered radiation has been maximized, this signal is coupled to a single, non-fiber detector 110 where it is processed to determine where particulates and other defects of the region 102 of the sample 101 are formed.

Figure 2B:
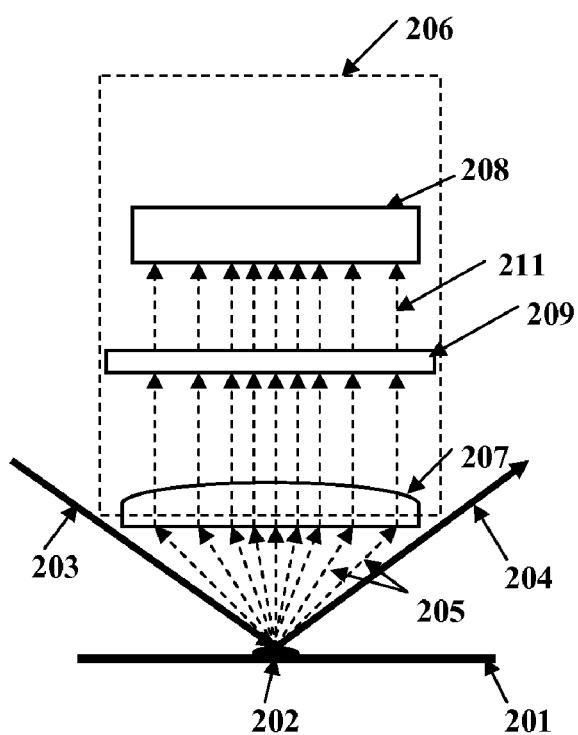
FIG. 2B is a diagram of a single collection system according to another embodiment of the present invention

Although in FIG. 2B, the collection systems 108 are only shown in a single plane, it is to be understood that such collection systems may substantially cover a hemisphere over the surface to be inspected.

FIG. 2B is a cross-sectional view of a collection system 200 as described in FIG. 1. A beam of monochromatic light 203 from a light source becomes incident on a region 202 of the sample 201. The incident beam 203 produces both specularly reflected light 204 and scattered radiation 205 from particulates, microroughness, and other defects. The collection system 206 acts to process this scattered radiation to determine the location of particulates and defects in the region 202 of the sample 201. The collection system contains a lens 207, a polarizing device 209, and a detector 208. The scattered radiation 205 is first focused onto the polarizing device 209 by the lens 207. Radiation 211 that is transmitted by the polarizing device 209 may be coupled to a single, non-fiber detector 208. The polarizing device 209 is divided into a plurality of polarizing segments, wherein each segment is characterized by a different polarization characteristic. The polarization characteristics are selected to transmit scattered radiation from particulates and other defects of the region 202 of the sample 201 and block noise from background sources including scattered radiation from microroughness of the surface of the sample 201 that does not share characteristics with the scattered radiation from particulates or other defects. By doing so, the signal-to-noise ratio (SNR) between the particulate scattering signal and the background sources of noise, which include surface microroughness, can be maximized, and particulates and other defects in the sample 201 may be more accurately identified. The polarizing device 209 is oriented to function optimally by using the well-known optical properties of a wafer with the same characteristics as our sample that is also known to be perfectly clean and calculating the expected scatter characteristics of the surface and the expected scatter of particle standards, such as PSL particles. The spatial-frequency distribution (PSD) of individual surfaces may vary to some degree, so the calculations may be somewhat inaccurate, but not by enough to negate its usefulness. Using a simulation tool, the polarizing device 209 may be divided into an appropriate number of segments, and the polarization pass axis of each segment is simultaneously varied, also allowing for segments to have no polarizer at all. The smallest particle standard that the polarizing device can reliably capture with each combination of polarizers and pass axes is calculated, and eventually the optimal polarizing device configuration is established. Once the SNR of the scattered radiation has been maximized, this signal from the detector 208 may be processed to determine where particulates and other defects of the region 202 of the sample 201 are formed.

Figure 3A:
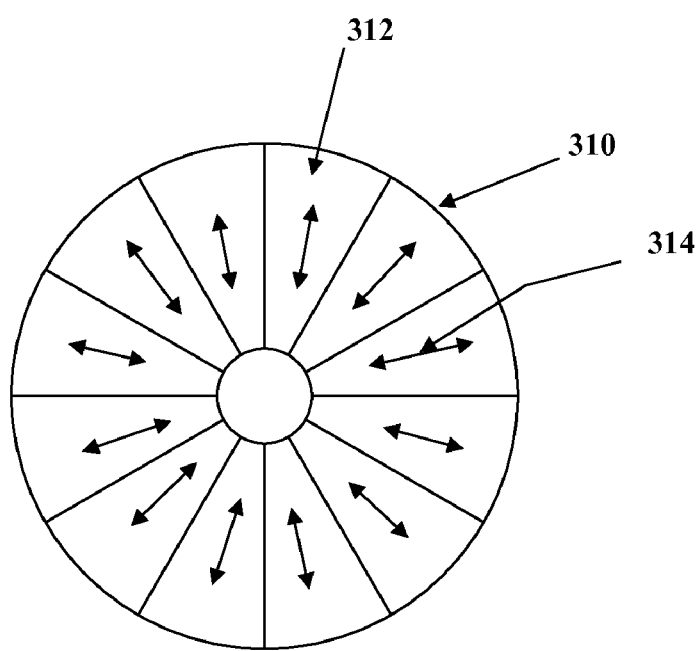
FIG. 3A is a diagram of the polarizing device of the prior art.
Figure 3B:
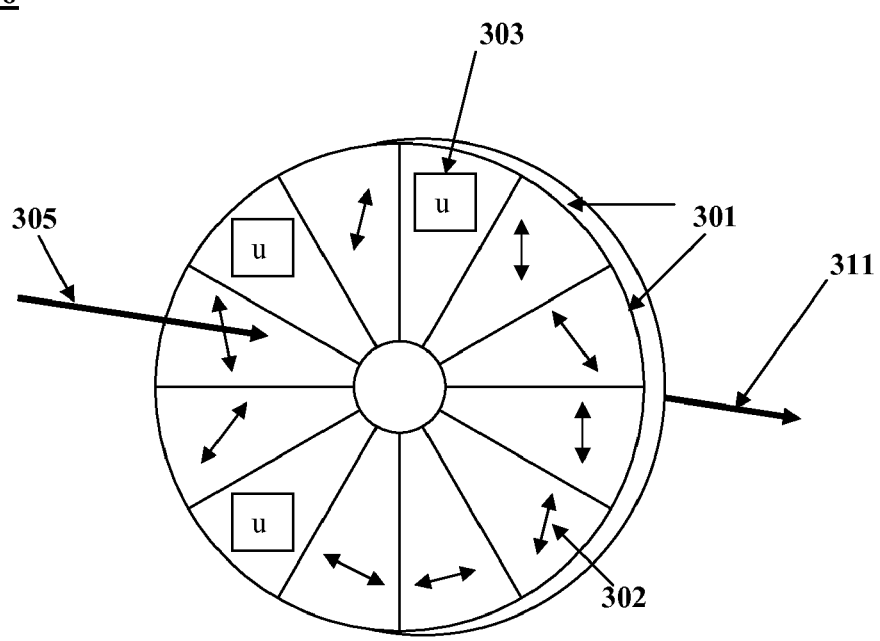
FIG. 3B is a diagram of the polarizing device according to an embodiment of the present invention.

FIG. 3B illustrates a top view of a polarizing device 300 that may be used as the polarizing device 99 described in FIG. 1, or as the polarizing device 209 described in FIG. 2B. This polarizing device 300 includes polarizing segments 301 each with a specific, fixed, pass axis of polarization 302 or no polarizer at all 303, denoted by "u". Each polarizing segment 301 with a specific pass axis of polarization 302 allows light of a polarization state corresponding to the specific pass axis of polarization 302 to pass. Each polarizing segment 301 with no polarizer 303, allows light of all polarizations to pass. Input light from a monochromatic source is incident on the sample. Interaction between the incident beam of monochromatic light and a sample produces output specularly reflected light and scattered radiation 305, which may be collimated and directed towards the polarizing device 300 and light 311 transmitted by the polarizing device may be detected by a detector to produce a signal. The purpose of the polarizing device 300 is to optimize the signal-to-noise ratio (SNR) for small particulates and other defects of the sample through appropriate orientation of the polarizing axes 302 of the polarizing segments 301. By optimizing the SNR, a polarizing device 300 will allow its corresponding sample inspection system to more accurately determine the particulates and other defects present in the sample.

By way of example, and not by way of limitation, the polarizing segments 301 may include one or more segments with polarization axes 302 configured to block noise caused by scattered radiation from microroughness or other noise sources that do not share characteristics with scattered radiation from particulates and other defects.

To calibrate the polarizing device 300 for optimal performance, a reference sample with the same characteristics as the sample of interest that is also known to be perfectly clean is chosen. This reference sample preferably has well-known optical properties at the wavelengths of interest. This makes it possible, in advance, to calculate the expected scatter characteristics of the surface, and the expected scatter of particle standards, such as polystyrene latex spheres (PSL particles). Using a simulation tool, the polarizing device 300 may be divided into an appropriate number of segments 301. Simultaneously, the polarization pass axis 302 of each segment 301 may be varied, also allowing for segments to have no polarizer 303. One can then calculate the smallest PSL particles that the system can reliably capture with each combination of polarizers and pass axes of polarization 302. Eventually, an optimal polarizing device configuration is obtained for which SNR is optimal or near optimal and capture rate is maximized. Obviously, the spatial-frequency distribution (PSD) of individual surfaces may vary to some degree, so calculations will be somewhat inaccurate, but not by enough to negate the usefulness of the polarizing device 300 and inspection systems that make use of the principle behind it.

Figure 3C:
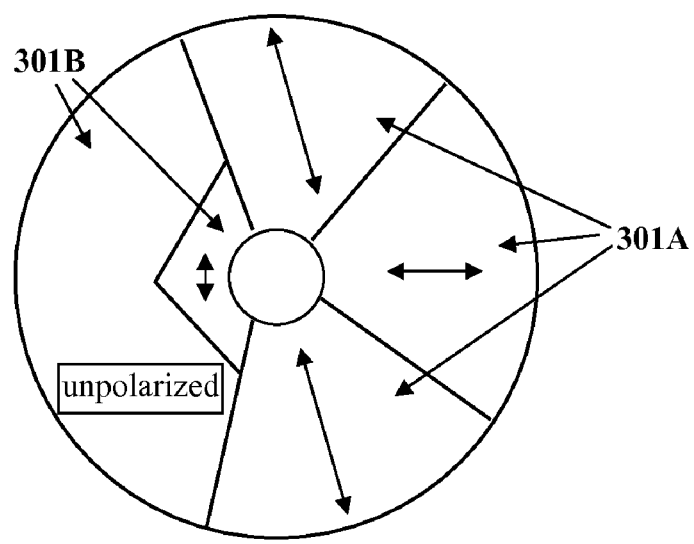
FIG. 3C shows a top view of another implementation of a polarizing device in accordance with an alternative embodiment of the present invention.

FIG. 3C shows a top view of another implementation of a polarizing device 300C in accordance with an alternative embodiment of the present invention. The polarizing device 300C is a variation on the configuration of the polarizing device 300 of FIG. 3B. The particular configuration shown in FIG. 3C involves two non-pie-shaped sections 301A and three pie-shaped polarizing sections 301B with appropriately oriented polarizing axes (indicated by double ended arrows). The configuration depicted in FIG. 3C is presented for the purposes of example but in no way restricts this invention. Any number and shape of polarizing sections may be used.

It is noted that a single polarizer configuration in a polarizer or system of the type described herein can work with one or more material types, depending on the material properties and inspection wavelength utilized. It is noted light scattered from the surface of a metallic material may be elliptically polarized. Consequently a simple linear polarizer, in general may not eliminate all surface scatter. On the other hand, using simple linear polarizers is a far simpler solution than also incorporating waveplates in each segment to convert from elliptical to linear polarization. It should also be noted that incorporating waveplates in each segment is also within the scope of embodiments of the present invention.

The reader's attention is directed to all papers and documents which are filed concurrently with this specification and which are open to public inspection with this specification, and the contents of all such papers and documents incorporated herein by reference.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A sample inspection system, comprising:
a) one or more collection systems that receive scattered radiation from a region on a sample surface proximate a symmetry axis of said collection systems and originating from an incident radiation directed at an oblique angle with respect to said sample surface, said collection systems being further configured to direct the scattered radiation to one or more detectors; and
b) a polarizing device disposed between said one or more collection systems and the detector, said polarizing device comprising a plurality of polarizing sections, wherein each section is characterized by different polarization characteristics,
said polarizing device being configured to transmit scattered radiation from defects to the detector and to block noise from background sources that do not share characteristics with scattered radiation from the defects from reaching the detector, wherein the polarizing device is configured such that a capture rate for the defects by the one or more detectors is maximized at a less than optimal signal-to-noise ratio.

2. The sample inspection system of claim 1, wherein the polarizing device includes a polarizer section configured to block noise caused by scattered radiation from microroughness or other noise sources that do not share characteristics with scattered radiation from particulates and other defects.

3. The sample inspection system of claim 1, further comprising:
c) a detector coupled to the collection systems, wherein the detector is screened from noise by background sources from reaching the detector while scattered radiation signals from particulates and other defects are allowed to reach the detector.

4. The sample inspection system of claim 3, wherein the one or more detectors includes one detector optically coupled to the polarizing device and a common collection system.

5. The sample inspection system of claim 3 wherein the detector includes a plurality of detector elements with each detector element being individually optically coupled to a different polarizing section of the plurality of polarizing sections by a corresponding collection system.

6. The sample inspection device of claim 1 wherein one or more polarizing sections of the plurality do not use a polarizer at all and allow light of any polarization state to pass through.

7. A polarizing device for use with a sample inspection system comprising:
a plurality of polarizing sections, wherein each section is characterized by a different polarization characteristic, wherein the polarizing characteristics are selected to:
a) transmit scattered radiation from defects;
b) block noise from all background sources that do not share characteristics with scattered radiation from particulates and other defects; and
c) maximize a capture rate for the defects by one or more detectors optically coupled to the polarizing device at a less than optimal signal-to-noise ratio.

8. The device in claim 7, wherein one or more polarizing section of the plurality do not use a polarizer at all and allow light of any polarization state to pass through.

9. The device in claim 7, wherein the scattered radiation from particulates and other defects includes scattered radiation from microroughness that shares characteristics with scattered radiation from particulates and other defects.

10. The device in claim 7, wherein the noise includes noise caused by scattered radiation from microroughness that does not share characteristics with scattered radiation from particulates and other defects.

11. A method for optically scanning a surface, comprising:

a) focusing a polarized beam of monochromatic light on a surface of a region of interest of a sample at an oblique angle of incidence, such that light is scattered in a plurality of directions;

b) collecting the scattered light with a collection system and directing the scattered light towards one or more polarizing devices said region and one or more detectors, wherein said one or more polarizing devices include one or more sections with specific, fixed polarizing axes of polarization or no polarizer at all, said polarizing devices having been configured to transmit scattered radiation from defects and to block noise from background sources that do not share characteristics with scattered radiation from the defects and maximize a capture rate for the defects by the one or more detectors at a less than optimal signal-to-noise ratio;

c) generating signals with the one or more detectors responsive to an intensity of scattered light incident thereon; and d) processing said signals to determine an optimal signal-to-noise ratio for particulates and other defects of said region.

12. The method of claim 11, further comprising; and e) repeating steps (a)-(d) with respect to each region of interest on said surface.

13. The method of claim 11, wherein noise from scattered radiation includes scattered radiation from microroughness of the surface of the sample that does not share characteristics with the scattered radiation from particulates and other defects of the sample.

14. The method of claim 11, wherein one or more polarizing sections of the plurality do not use a polarizer at all and allow light of any polarization state to pass through.

15. The method of claim 11, wherein the scattered radiation from particulates and other defects includes scattered radiation from microroughness that shares characteristics with scattered radiation from particulates and other defects.

16. The method of claim 11, wherein the noise includes noise caused by scattered radiation from microroughness that does not share characteristics with scattered radiation from particulates and other defects.

17. The method of claim 11, wherein the one or more detectors includes one detector optically coupled to the polarizing device and a common collection system.

18. The method of claim 11 wherein the detector includes a plurality of detector elements with each detector element being individually optically coupled to a different polarizing section of the plurality of polarizing sections by a corresponding collection system.

* * * * *